United States Patent [19]
Rasor et al.

[11] 3,943,936
[45] Mar. 16, 1976

[54] SELF POWERED PACERS AND STIMULATORS

[75] Inventors: Ned S. Rasor, Kettering; Joseph William Spickler, Maumee, both of Ohio

[73] Assignee: Rasor Associates, Inc., Sunnyvale, Calif.

[22] Filed: Oct. 9, 1973

[21] Appl. No.: 404,764

Related U.S. Application Data

[62] Division of Ser. No. 73,809, Sept. 21, 1970, Pat. No. 3,835,864.

[52] U.S. Cl. ......... 128/419 P; 128/418; 128/419 B; 128/419 PG; 128/419 PS
[51] Int. Cl.² ............................................ A61N 1/36
[58] Field of Search.. 128/404, 418, 419 B, 419 PG, 128/419 R, 421, 422, 2 M, 2.05 R, 303 R, 343, 348, DIG. 9, 325, 260, 264, 267, 268

[56] References Cited
UNITED STATES PATENTS

| | | | |
|---|---|---|---|
| 1,006,341 | 10/1911 | Ammons | 128/264 |
| 3,486,506 | 12/1969 | Auphan | 128/419 P |
| 3,540,431 | 11/1970 | Mobin-Uddin | 128/325 |
| 3,563,245 | 2/1971 | McLean et al. | 128/419 P |
| 3,649,367 | 3/1972 | Purdy | 128/419 P |
| 3,683,933 | 8/1972 | Mansfield | 128/419 P |
| 3,737,579 | 6/1973 | Balduc | 128/419 P |

OTHER PUBLICATIONS

Myers et al., "American Journal of Medical Electronics," Oct.–Dec., 1964, pp. 233–236.

*Primary Examiner*—William E. Kamm
*Attorney, Agent, or Firm*—Jerome P. Bloom

[57] ABSTRACT

A stimulator device for insertion in a living body, having particular advantage for intracardiac use comprising a housing having a body formed for transvenous or transarterial insertion, electrode means at the outer surface of said body, means included in said housing defining a pulsing circuit electrically connected with said electrode means and means for activating said pulsing circuit embodied in said housing, said activating means being free of physical connection with an outside power source and dependent for its function on the living body in which it is inserted.

14 Claims, 14 Drawing Figures

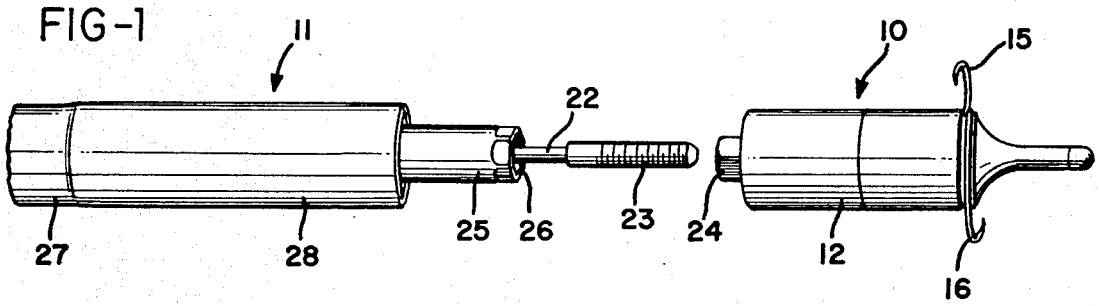
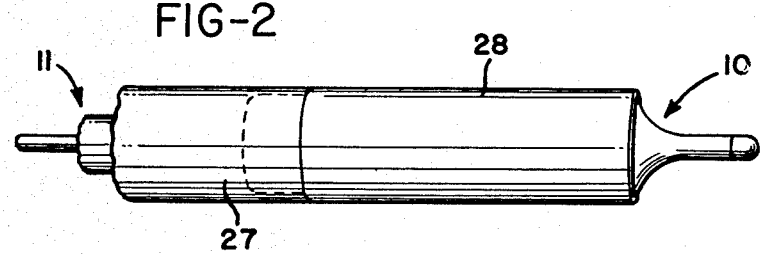
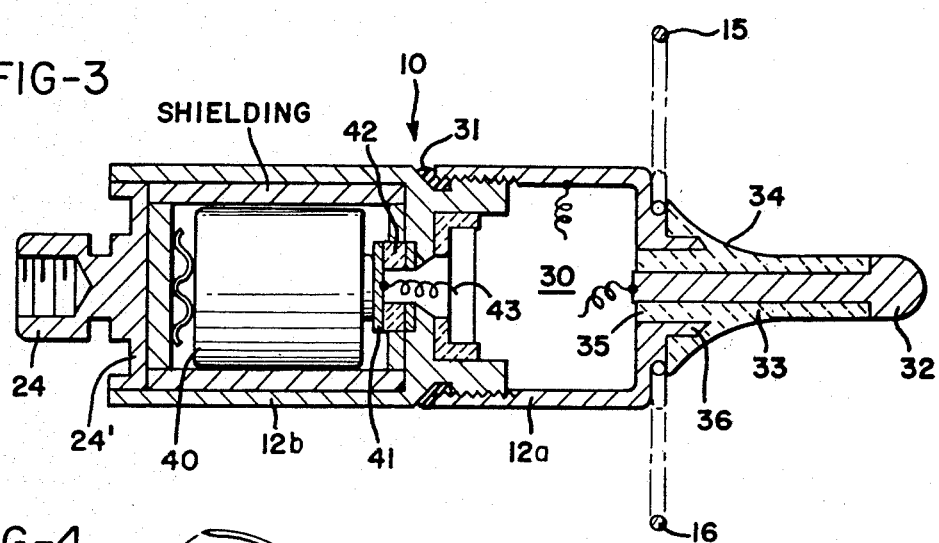
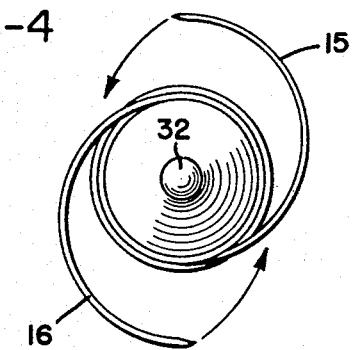

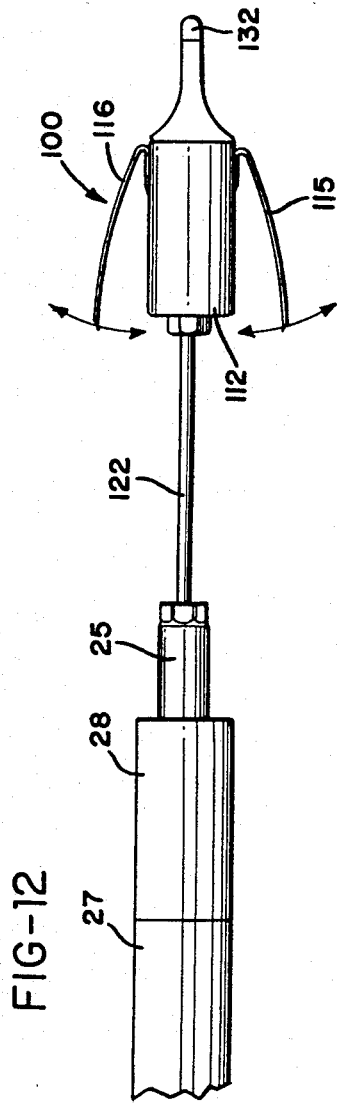

SELF POWERED PACERS AND STIMULATORS

This application is a division of applicants' co-pending application Ser. No. 73,809, filed Sept. 21, 1970, now U.S. Pat. No. 3,835,864 for SELF CONTAINED BIOELECTRIC STIMULATOR.

BACKGROUND OF THE INVENTION:

Implanted "Pacemaker" devices are now commonly employed for the long-term treatment of atrio-ventricular (A-V) block. Such pacemaker devices commonly employ flexible leads which connect a remotely positioned power pack with electrodes which are placed in contact with or attached to the myocardium. The techniques of implanting and using such pacemakers, and many pacemakers which have been used experimentally and in practice, are described in Siddons and Sowton, Cardiac Pacemakers (1967), published by Charles C. Thomas, Springfield, Illinois, Library of Congress Card No. 67-12042. Pacemakers having energy sources responsive to heart movement are shown in U.S. Pat. Nos. 3,358,690 and 3,486,506.

Such Pacemakers, or other biological stimulators working on these principles, have inherently suffered from certain disadvantages. The leads to the electrodes are commonly routed through veins leading into the heart itself. The movement of the heart and normal activity of the individual tend to put a strain on these leads and may result in lead breakage or dislodgement of the electrodes. The leads themselves, retained in situ, are frequently a source of irritation and infection. Further, since the electrical contact with the heart is made at the point or region of mechanical support or implantation, the normal fibrosis of tissue at these regions often results in marked increase of power required to pace, known as an increase in threshold. For example, the threshold has been found to increase on the order of ten times its original value until a plateau is reached over a period of two to three weeks. This requires a correspondingly greater power input to the electrodes, in the minimum of 3:1 over threshold, in order to achieve consistent pacing.

The remote power pack itself is a cause of discomfort and often a cause of difficulty. It is commonly implanted in a subcutaneous pocket beneath the pectoralis major or within the abdomen. Again, this provides a further opportunity for infection. Difficulty has also been encountered in preventing migration of the power pack. Further, surgery is required from time to time to expose and replace the power pack due to exhaustion of the mercury cells.

Prior pacing devices which derive their energy from the heart movement or pressures have commonly required thoracic surgery for attachment to the epicardium, and have employed flexible leads to the electrodes.

SUMMARY OF THE INVENTION

The present invention is directed to a cartridge type wholly self-contained stimulator unit which integrates its own power source and is particularly adapted for use as a stimulator or pacer. The entire structure including the powe source is contained within a package or housing which is sufficiently small to be implanted in a living body, for example as by transvenous or transarterial insertion into the chamber of the heart where it is attached to the endocardium. The stimulating electrodes are formed integrally with the unit, and thus make contact with the endocardium.

A pacemaker device made according to the present invention is intended primarily for long-term use. It can be used without discomfort to the user. The likelihood of a failure due to dislodgement of electrode contact, increase of threshold, or occurrence of infection is substantially reduced. In view of absence of leads, failure due to electrode lead breakage is eliminated entirely. The device can be implanted by means and technique which require only minor surgery and temporary discomfort to the patient. It can be recovered if desired or, if failure should occur, it may simply be left in place and a new device inserted.

In one form of the invention embodiment a nucleonic battery is employed to provide a power source to the pulse generator circuits contained therewith within the unit housing. Such a battery can provide for an overall life of the unit which may be well beyond the normal life expectancy of the patient. For example, a Pu-138 battery has a half life of 86 years, while Pm-147, which may be preferred because of lower costs, has a half life of 2.7 years. Suitable electronics in the converting and pulse generating portion can operate efficiently over three or more half lives. Operation over such a large power range is made possible in part by the fact that the device of the present invention does not cause a material or significant increase in threshold, and therefore can continue to operate after decay to very low power levels.

Three illustrative forms of embodiment of the invention herein disclosed employ a biologically energized power source and thus derive their power requirements from the body itself. Prior art devices of this nature have obtained insufficient power from normal heart activity to provide reliable and continuous pacing. However, use of apparatus of the present invention does not result in a significant increase in threshold power and accordingly provides reliable pacing over an extended period of time with modest lower power requirements. Per the present invention embodiment, the energy required for each stimulation pulse may be in the order of one microjoule or less, corresponding to a total power input to the electronics on the order of six microwatts or less, whereas the energy requirement for heretofore available apparatus substantially exceeds this.

In one form of the invention embodiment, a movable wall or diaphragm transforms hemodynamic pressure into electric energy by means of a suitable transducer. In other forms of embodiment, a mass is suspended in such a manner that movements of the heart set up a sympathetic or harmonic movement of the mass, which is electromechanically coupled to produce energy. For example, the transducer may comprise a permanent magnet in combination with a non-moving electric coil. In another form, the mass may be connected to stress a piezoelectric crystal.

In preferred embodiments the unit housing structure of the present invention may also be used as the electrode structure for the pacers or stimulators, in a manner to offer certain advantages over the endocardial electrodes which are presently in use.

It is the primary objective of the invention to provide stimulator or pacer devices which can function free of external leads or connections.

Another important object of the invention is the provision of a stimulator or pacer device which is fully self-contained and implantable in a cartridge form for function and generation of power to make it function at the site of stimulation.

A further object of the invention is the provision of a self-contained stimulator or pacer packaged in a form as to permit a safe insertion thereof into passages, chambers or organs of a living body.

A further object of the invention is the provision of a self-contained intracardiac pacemaker which employs either a nucleonic power source or a biologically activated power source and is adapted to function over an extended period of time without the necessity of attention by a physician.

Another important object of the invention is the provision of a self-contained, self powered implantable pacer or stimulator which is adapted to be received in its entirety within a heart chamber with electrodes formed on the outer portion thereof wherein the power may derive its source from hemodynamically movable portions, suspended masses or fuel cells embodied in the structure housing.

A further object of the invention is the provision of a novel manipulator apparatus for inserting a pacer or stimulator in a living body. The manipulator is preferably comprised of three concentric elements in a triaxial arrangement. One of the elements is removably secured to the housing of the stimulator device, a second element forms a torque tube which may be used to assist in implanting the device and for removing the first element from the device, and the third element comprises an outer removable sheath which preferably extends at least partially over the body of the device during transvascular passage and may be employed to retain the body-attaching members on the device in a retracted or inoperative position until the device has been positioned, as desired. Thereafter, the sheath may be retracted to expose the body or tissue-attaching members, or extended to cover these members for removal of the device from the heart.

Another object of the invention is the provision of an internal, self-contained and retrievable pacemaker.

These and other objects and advantages of the invention will be apparent from the following description, the accompanying drawings and the appended claims.

BRIEF DESCRIPTION OF THE DRAWINGS:

FIG. 1 is an exploded view of the stimulator and manipulator devices of the invention;

FIG. 2 shows parts of FIG. 1 in assembled condition;

FIG. 3 is an enlarged sectional view, partially in diagrammatic form, of the stimulator of FIG. 1 adapted particularly for use as a heart pacer;

FIG. 4 is an end view of the device of FIG. 3;

FIG. 12 is a modified manipulator and improved pacemaker electrode assembly according to the teachings of this invention.

Figure 5A:
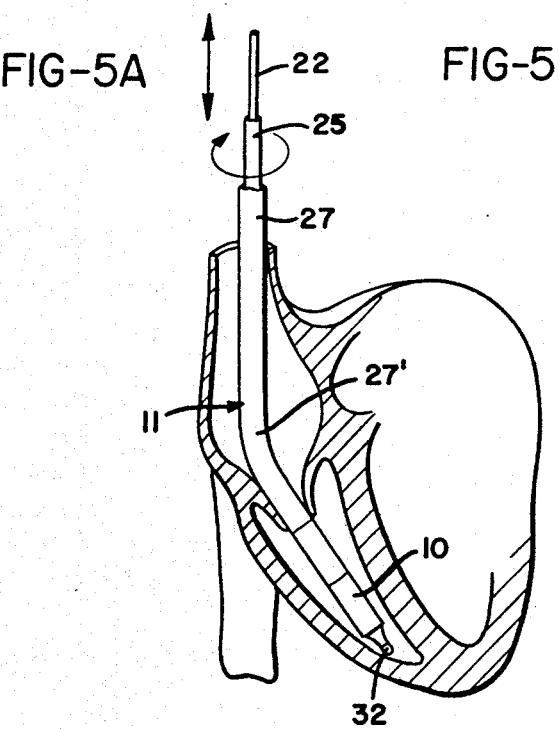
FIGS. 5a, 5b and 5c are, respectively, diagrams illustrating the method of implanting the pacer using the manipulator device of this invention.

DESCRIPTION OF PREFERRED EMBODIMENTS:

FIGS. 1–4 reveal a self-contained unit 10 of cartridge-like form providing a stimulator or pacer device in accordance with the invention, particularly adapted for use as a heart pacer. In association therewith is a manipulator 11 adapted for its application and removal. The device 10 is embodied in an elongated capsule-like generally cylindrical housing 12.

Preferably, the outer surfaces of housing 12 are formed exclusively of biologically compatible materials, the major portion of which may be stainless steel. While the outer surface of the body 12 is shown as formed essentially of smooth inert material, such as stainless steel, it is within the scope of this invention to provide the body with a compatible flocking material, such as a dacron weave, to promote the formation of neointima once the device has been implanted.

The device can be implanted in any of the four chambers of the heart where patho-physiology would be optimum for a particular patient. However, the description of the illustration will emphasize its implantation within the right ventricle where the greatest clinical and experimental experience has been concentrated to date. When the stimulator or pacer device 10, is adapted for implantation directly within a heart ventricle, it should have a maximum overall length not substantially exceeding 30 mm and preferably in the order of 18mm or less. The diameter of the body 12 should not substantially exceed 10mm and is preferably 8mm or less. Such dimensions provide a capsule type unit which is sufficiently small to permit its transvascular insertion into a ventricle, without disturbing the proper function of the heart.

The forward end of the housing 12 is provided with means for attaching the stimulator or pacer 10 to the myocardium. A preferred form of the attachment means comprises a pair of oppositely directed spiral stainless steel attaching means comprising barbs or wires 15 and 16, as best shown in FIG. 4. The wires have inner ends attached to the circumference of the housing 12 and outer ends which are free and projectable from the housing. These attaching wires are adapted to be retained in a retracted position in closely surrounding relation to the circumference of the housing 12, but they are capable, when released, to spring out to the expanded or operative position, as shown.

Manipulator means for transvenous implanting of the stimulator or pacer device 10 preferably consists of the triaxial device illustrated generally at 11 in FIGS. 1 and 2. This structure comprises a central rod 22 formed with a threaded end 23 which is adapted to be attached or received within a suitable internally threaded nut 24 formed on the rear wall 24' of the housing 12, as shown in FIG. 3. A torque tube 25 slidably received over the rod 22 is formed at its forward end with an internal socket portion 26 adapted to position over and about the nut 24 to be placed thereby in driving engagement with the Pacemaker 10. The manipulator 11 is further provided with an axially slidable sheath 27 including a forward metallic end portion 28 of a diameter sufficient to telescope, at least partially, over the rear end of the housing 12 of the pacer 10. In use, the sleeve 28 substantially covers the housing 12 to retain the attaching wires 15 and 16 in their retracted position, substantially as shown in FIG. 2. The use of the manipulator 11 is further described in connection with the description of illustration of FIGS. 5a–c.

The entire manipulator apparatus may be rigid with defined bends or may be flexible or may be steerable. In the preferred form, the central rod 22 and the torque tube 25 are flexible, while the forward end of the sheath 27 is formed with a predetermined bend, as indicated at 27' in FIG. 5a. The bend which may be formed within 2–4 inches of the end of the manipulator assembly, may have an angle of approximately 30° in order to permit the manipulator and the attached pacemaker to be steerable around corners and bends.

Figure 6:
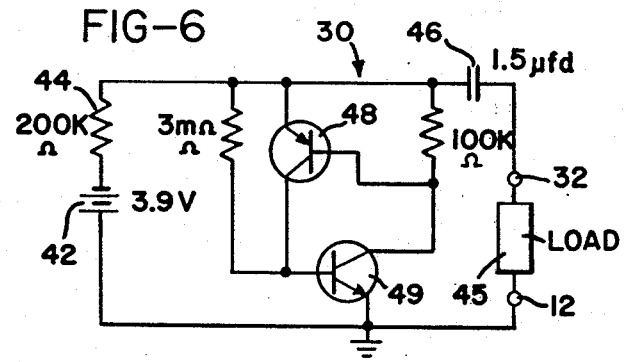
FIG. 6 is a schematic drawing showing a pulsing circuit which may be used with this invention.
Figure 7:
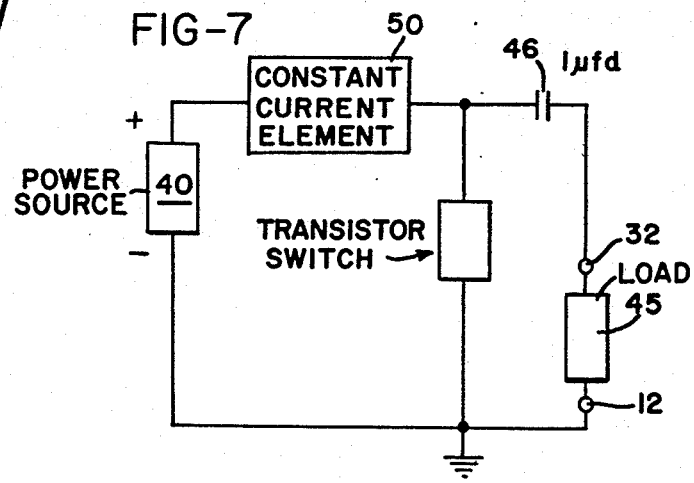
FIG. 7 is a diagram of a modified form of the circuit of FIG. 6 particularly adapted for use with a nucleonic or other varying power source.

Referring particularly to FIG. 3, the unit providing the invention stimulator or pacer device 10 is shown as including a forward housing portion 12a and a cylindrically continuous rear housing portion 12b. The forward portion 12a is hollow and contains the electronic plusing circuit 30, illustrative examples of which are shown in FIGS. 6 and 7. It has been found that relatively simple circuits as here illustrated are totally satisfactory and are in fact preferred over the more complicated circuits such as shown in the reference text referred to under the Background section of the specification. The simpler circuits such as here provided generally have lower losses and greater overall reliability. Such circuits can easily be fitted within the cavity defined with the housing section 12a without the necessity of reverting to microminiature or integrated circuits. However, such circuits permit even further miniaturization, but the overall size of the stimulator of this invention is dictated not so much by the circuit requirements but by the space requirements of the power source.

The housing sections 12a and 12b may be threaded together and sealed as shown at 31, but it is within the scope of this invention to make the housing 12 of simple one-piece construction. The rear wall 24' is preferably welded to the case 12b by electron beam welding. There is some advantage in the two-piece construction of FIG. 3 in that it permits the housing parts to be separated and adjustments to be made to the circuit prior to insertion.

One of the important advantages of the stimulator of the present invention resides in the fact that the pacing electrodes are formed to be integral with outer surfaces of the housing 12. To this end, the housing portions 12a and 12b themselves define the positive pulsing electrode which, as previously noted, may be formed preferably of stainless steel. The negative pulsing electrode 32 is formed preferably of platinum and supported on a forwardly extending dielectric pedestal 33. The pedestal is preferably formed of an inert ceramic, defining a hollow co-axial insulator. The insulator 33 may thus have an outer curved surface 34 leading smoothly from the stimulating electrode 32 and flaring outwardly at the housing portion 12a to assist in guiding the stimulator device during insertion. A tubular portion 35 extends into the interior of the housing portion 12a, forward end of which is formed with an annular ledge 36 to provide support for the insulator and for the electrode 32.

The stimulating electrode 32 may also be of the differential current density type, known as the "Parsonnet Electrode" and described by George H. Myers and Victor Parsonnet in Engineering in the Heart and Blood Vessels, (1969) John Wiley & Sons, New York, N. Y.

The pacer construction shown in the preferred embodiment illustrated has several important advantages. In the first place, it will be noted that, unlike prior stimulators, the electrodes in this case do not themselves form or comprise attaching devices. In fact, the stimulating electrode is well spaced from the attaching points of the wires or barbs 15 and 16. Thus, once the stimulating electrode has made reliable pacing contact with the heart tissue, it does not transmit the destructive forces of attachment and retention to this tissue. The vicinity of the pacing contact thus remains free of the adverse effects of fibrosis which invariably occurs at the regions of attachment or forcible retention.

In devices where electrodes themselves are directly attached or are forcibly retained by pressing against the tissue, an approximately 10 times increase in the threshold is not uncommon. This occurs over approximately a two to three week period subsequent to implanting and then reaches a plateau. Such a substantial increase in threshold requires a corresponding increase in power requirements simply to overcome the threshold and to effect reliable stimulation. By the present construction and the consequent elimination of the cause of threshold rise, one achieves reliable pacing with substantially lower power consumption.

An important advantage of the unit construction of FIG. 3 is the total elimination of external flexible leads between the pacing circuit and the tissue to be stimulated. This then results in the elimination of lead placement and breakage difficulties and mechanical load problems normally incident to usage of leads as provided in prior art pacers.

A further important advantage of the pacer of this invention is the fact that it can be reliably powered from a suitable nucleonic power source 40. There are available in the present state of the art a number of nucleonic conversion devices which may be contained within the physical dimensions of the housing portion 12b, and suitably shielded and sealed therein. A preferred form of such device is a betavoltaic converter which is, in effect, a stack of semiconductor photocells which are coated with a radioactive material and which are irradiated by beta particles to produce an unidirectional current electric output. Beta sources may include Pm-147 which has a 2.7 years half life. It is within the state of the art to provide an electronic circuit which will operate effectively over more than three half-lives of such power sources within the volume available. The use of tritium, with a half life of 12.6 years, is also possible.

A power source 40 using radioisotope fuel may also be of the thermionic type, the thermoelectric type or the double conversion type. In the thermionic and thermoelectric types, heat from the radioisotopic fuel is transformed into electric power by electron transport through a thermionic diode or thermocouple respectively. In the double conversion type, radiation from the radioisotope fuel is employed to excite a light-emitting phosphor, and the photons in turn excite a semiconductor photocell. All three of these types can use Pu-238, which is a desirable fuel for biological applications and has a half life of 86 years. The choice of fuel and type of convertor will depend upon the cost of the source material and fabrication, the half life, and the efficiency of conversion as well as the shielding required. Suitable radioisotopefueled batteries are made by Donald W. Douglas Laboratories, 2955 George Washington Way, Richland, Washington and sold under the tradenames "Betacel" and "Isomite", representing beta-voltaic and thermionic types respectively. While nucleonic power sources are preferred by reason of long life, it is within the scope of the invention to employ rechargeable batteries, or mercury cells. The latter may be satisfactory for short term pacing, in view of the relatively high overall efficiency of the device.

As shown in FIG. 3, an insulated plate 41 in contact with the power source is hermetically sealed by an insulator 42, and leads 43 extend to the circuit contained within the housing section 12a. The case 12 is negative with respect to the power source but is positive with respect to the biological load.

The diagram of FIG. 6 illustrates one form of the pulsing circuit in which a power source 42 is shown as providing an output voltage of approximately 3.9 volts. This output as applied through charging resistor 44 and through the load 45 to a capacitor will depend upon the charging time constant of the circuit, and since the biological load 45 is normally less than 1,000 ohms it forms a small part of the total resistance in the charging circuit. However, as long as the load 45 is present the circuit will charge.

The transistors 48 and 49 comprise a transistor switch. This switch automatically becomes conductive to connect one side of the capacitor 46 to ground at some predetermined potential during the charging of the capacitor 46, and thus provides a low impedance grounding circuit permitting a discharge of the capacitor through the load 45. The peak load voltage may be 1.3 volts, and the transistor switch may be conductive for 3ms. Thereafter, the current through the switching circuit drops to the point where it becomes non-conductive, and recharging of the capacitor 46 resumes through resistor 44, at a repetitive rate depending on the R-C constant.

It might also be noted that since the capacitor 46 is charged through the biological load a current reversal takes place between the negative pulsing electrode 32 and the case 12 which has the effect of reducing or eliminating polarization which otherwise occurs when electrodes are pulsed in the same direction in an electrolytic solution.

The diagram of FIG. 7 is essentially for the same circuit as shown in FIG. 6 except for the addition of a constant current element 50 which may comprise a constant current transistor. This circuit is useful to maintain a constant pulse height and rate when the pulsing circuit is used with nucleonic power source whose output decays with time, or with biologically activated power sources whose output varies with the amount of biological activity.

The method of implanting the stimulator or pacer unit of the present invention using the improved manipulator is illustrated diagrammatically in FIG. 5. The unit pacer is assembled with the manipulator 11 as shown in FIG. 2. The manipulator is formed with a fixed or predetermined bend 27' about two to three inches from the end, of about 20°-40°, to enable it to turn corners while it is being inserted. The insertion technique itself is essentially the same as currently in use for the transvenous implantation of endocardiac electrodes and other cardiac catherization procedures. The pacer may, for instance, be inserted in the right external jugular vein and advanced through the superior vena cava and through the right atrium into the apex of the right ventricular cavity. This is the position illustrated in FIG. 5a. This is accomplished, of course, under fluoroscopic observation.

Prior to attaching the pacer unit, the effectiveness of its resting position may first be observed with an electrocardiograph to assure that it is functioning normally and that it has captured the heart. The end 28 of the sheath 27 is preferably made of conductive material, such as stainless steel, so that the electrode formed on the body 12 will conduct through the sheath.

Figure 5B:
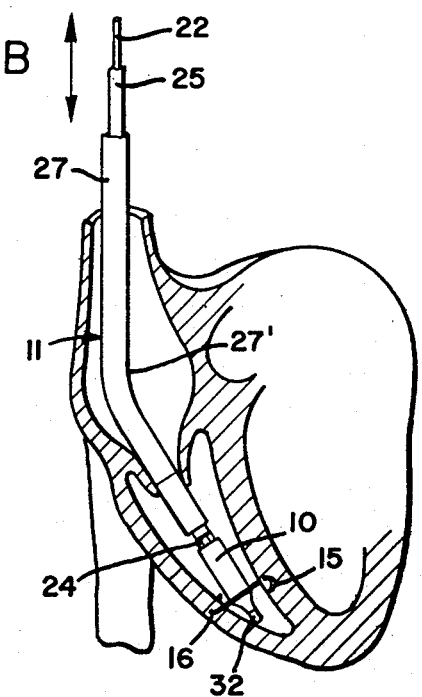

Having determined a proper position, the sheath may be partially retracted as shown in FIG. 5b to expose the barbs, and the torque tube 25 rotated clockwise to imbed the barbs in the myocardium. The entire pacer unit, in this condition, will be wedged into the trabeculae making contact both with the case and with the tip electrode 32.

Figure 5C:
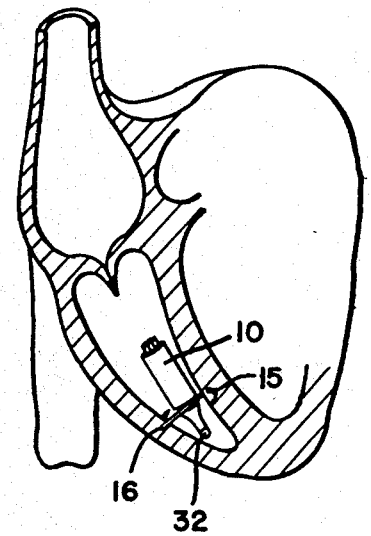

Once attachment in this manner is made, the torque tube 25 may be held against rotation and the rod 23 unscrewed from the internal threads in the nut 24. The entire manipulator may then be extracted leaving the pacer unit imbedded essentially as shown in FIG. 5c. The pacer unit can be extracted from the heart by reversing the foregoing procedure.

The invention is not limited to heart pacing as such. Other examples of applications of the self-contained stimulator or pacer unit where there is direct implantation at the site of the stimulation without separate electrical leads include baropacing (stimulation of the baroreceptors in the neck or aortic arch), stimulation of the diaphragm for breathing (stimulation of the phrenic nerve), stimulation of the numerous sphincter muscles which control the flow of various body fluids and solids (at the sphincter site), and other such functions which have been shown to respond to electrical stimulation and which small size of the stimulator and absence of electrical leads would render feasible or more practical. In most such cases the self-contained stimulator described in FIG. 3 would deliver a pulse approximately every 20 milliseconds during activation of the biological function instead of about one pulse per second as in the cardiac pacer. Activation of the pulse train could be accomplished by external command via an electromagnetic or magnetic signal from outside the body.

Figure 8:
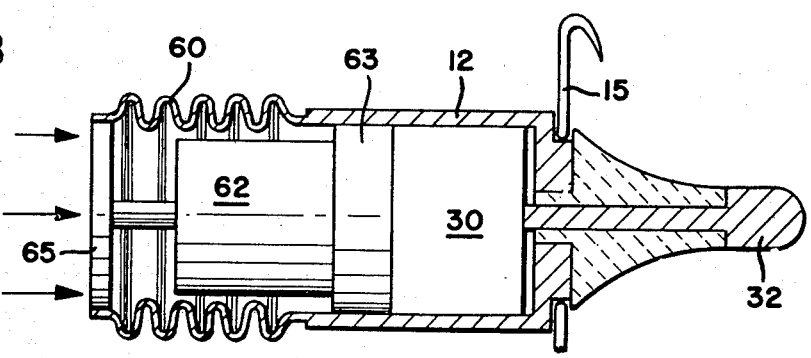
FIG. 8 shows a modified form of the invention adapted to respond to hemodynamic pressure changes.

The invention is not limited to an arrangement which contains an internal source of power. In FIG. 8 there is illustrated an embodiment of the invention which is responsive to hemodynamic pressure. The housing section 12b is replaced by a flexible or movable section which incorporates a rubber diaphragm or metal bellows 60 which moves under the influence of pressure changes within the heart cavity. Forces and motions arising from such pressure changes are applied to an electromechanical transducer 62 the output of which may be applied to a suitable energy storing circuit 63. The transducer may be of the magnetic induction type or may be a piezoelectric generator. The storage device 63 may be a diode-isolated full-wave rectifier with capacitor storage. The energy thus stored is available for subsequent release to the stimulation electrodes by a pulse forming circuit substantially as previously described. The storage device will be kept charged by the succession of heart beats and therefore serves the function of the power source previously described.

For example, if the effective area of the movable section 65 is about ½cm², and moves 1mm under the influence of a 20 torr average pressure pulse, each beat would produce about 130 microjoules of mechanical work. Since less than 10 microjoules of electric energy is required for each pulse, a large margin of reserve power is available.

Figure 9:
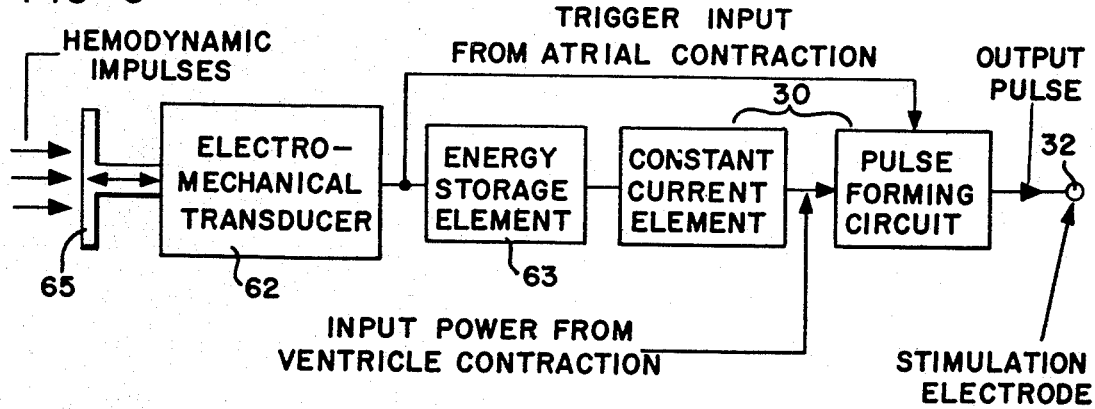
FIG. 9 is a block diagram of the pacer of FIG. 8.

A circuit diagram at FIG. 9 shows an arrangement of the pacer of FIG. 8 adapted as a synchronous pacer, to obtain the benefits from synchronous pacing by slaving the unit to the atrial systole. After storing the large power pulse generated by the transducer during the ventricular contraction, the pulse-forming circuit is "armed"; i.e., it reaches a condition in which the next significant electrical signal from the transducer will cause the circuit to "fire" and deliver an electrical pulse to the stimulating electrodes. Therefore, the pressure impulse from the next atrial contraction is transmitted through the tricuspid valve to generate an electrical signal from the transducer which fires the circuit. The stimulated ventricular contractions thereby become synchronized with the atrial contractions. It may be desirable to construct the circuit so that "arming" is delayed until after the refractory period of the heartbeat to avoid premature firing by reverberations from the ventricular contraction. Also it may be desirable physiologically to provide a delay between the signal from the atrial contraction and the pacer output pulse, similar to the delay in the A–V node.

Figure 10:
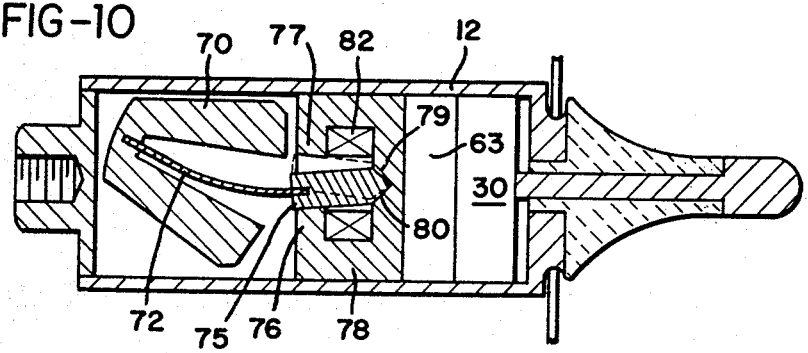
FIG. 10 is a further modification showing a biologically powered pacer according to the present invention.
Figure 11:
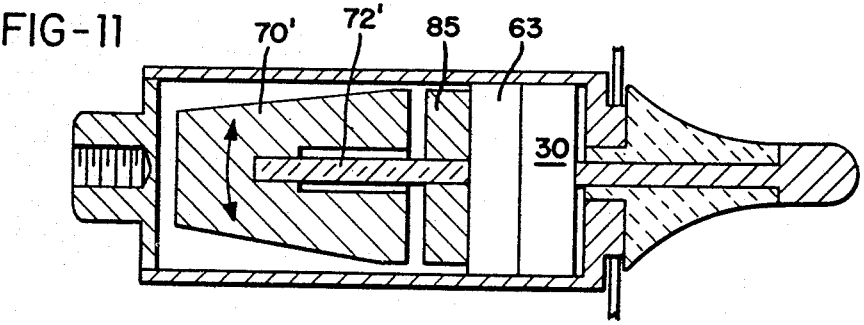
FIG. 11 is a still further modification showing another form of the biologically powered pacer.

FIGS. 10 and 11 illustrate additional arrangements by means of which the heart movement itself can be used to provide a suitable source of energy. Observation has shown that an implanted pacer undergoes transient displacements of about 1cm within a 24th of a second. Assuming constant acceleration, a 5mm displacement relative to the capsule over 1/24th second of an armature weighing 4 grams would produce a force of about 2500 dynes acting over this distance, to produce about 120 microjoules of work per beat, again substantially in excess of the requirements of the pacer. Referring to FIG. 10, a mass 70 is mounted in the manner of a pendulum on the end of a leaf spring 72. The natural oscillation rate of the mass 70 on the spring 72 may be that of the paced heart rate. The lower end of the spring 72 is joined with a magnetic armature 75 received between the poles 76 and 77 of a permanent magnet 78.

The lower end of the armature is retained in a V-shaped recess 79 by the magnetic attraction and is correspondingly formed with a knife or V-edge 80 to provide a pivotal movement. The poles 76 and 77 are spaced apart so that the armature 75 can assume either one of two stable positions, as shown by the full lines and broken lines. In one position, the flux is induced through the armature in one direction while in the other position it is induced in the opposite direction.

Since the pendulum formed by the mass 70 and spring 72 oscillates in resonance with the sinus rate of the heart, the bending moment of the spring 72 lifts the armature 75 from one pole face whereupon it abruptly moves to the opposite pole face, resulting in a sudden reversal of the flux and inducing an electric current in the surrounding coil 82. The coil output may be applied to the storage device 63, as described in connection with FIG. 8. FIG. 11 is similar to FIG. 10 except that the mass 70' and the spring 72' are connected to stress a piezoelectric crystal 85. In this embodiment, the periodic rate of the mass and spring may be substantially greater than that of the heart, to produce a "ringing" effect with each beat.

Certain of the teachings and advantages of the present invention may be used to improve the performance of existing pacers which presently use endocardial electrodes. The body pacer 10 may be modified for this purpose to perform the function of the electrodes only and an arrangement for this purpose is illustrated at 100 in FIG. 12. In this case, the cartridge housing 112 is made similarly to the housing 12 except that it does not contain any pulsing circuitry or power source, but merely comprises means for making electrical contact. Thus, the housing 112 may conveniently be made to a smaller length and/or diameter than that which has previously been described. The outer surface of the housing 112 thus comprises one of the electrodes, while stimulating electrode 132 may be made and supported on a ceramic pedestal spaced from the housing 112 in the manner which has been described in connection with the electrode 32 of FIG. 3.

The electrode assembly 100 will be connected by flexible leads to a conventional remote pulsing device by means of a flexible electrical conduit or lead 122. The lead 122 may be of a coaxial conductive cable, which has one of its leads connected to the case or housing 112 and the other connected to the electrode 132. The assembly 100 may be used with remote pacers which employ a single electrode lead or a pair of leads. Where a single lead is used, it would be connected inside the housing 112 to the electrode 132.

The electrode assembly of this invention is provided with a somewhat modified form of attachment comprising a pair of generally axially extending retaining wires 115 and 116. The forward ends of the wires are attached or secured to the housing 12. The wires extend rearwardly and outwardly, and are movable between a retracted position in which the wires lie adjacent to the outer surface of the housing, to a spread apart position, substantially as shown.

The general technique of inserting and implanting the electrode assembly 100 does not differ substantially from that described in connection with the pacer unit 10. The torque tube 25 and the sheath 27 may be used, with the rod 22 removed. The cylindrical conductive end 28 would be received partially over the housing 112 with the attaching wires 115 and 116 collapsed and retained within end 28. The electrical lead 122 is threaded through the hollow torque tube 25.

It would be expected that the electrode assembly would be inserted well into the apex of the ventricle cavity accompanied by some stretching of the heart muscle. The torque tube 25 could be employed to provide axial forces as well as rotational alignment. The sheath 27 would then be retracted exposing the ends of the attachment wires 115 and 116, and when the axial force is released the ends of the wires would tend to imbed themselves within the heart muscle. If necessary, some pull could be placed on the lead 122 to complete the attachment, and then the manipulator may be extracted leaving the electrode assembly 100 in place.

The electrode assembly 100 provides to a remote pacer certain of the advantages of the present invention. Principally, the electrodes, which are formed as integral and discrete surface portions of the assembly, are not prone to dislodgement, movement, penetration or breakage. Further, they define regions of stimulation which are spaced from the region of attachment, as in the case of the pacer 10, and thus remain free of the adverse effects of fibrosis.

It is accordingly seen that this invention provides on the one hand a novel self-contained, self powered biological stimulator unit, which is particularly adapted for use as a pacer per se, and an electrode assembly useful with existing pacers. It is intended for long-term treatment of partial or complete A–V block. Synchronous pacing may be used, as desired, and the circuit can be modified as known in the art for demand pacing. For synchronous pacing of devices of the types of FIGS. 3, 10 or 11, a short sensing or trigger electrode wire may extend axially from the rear wall 24' of the body 12b through the tricuspid valve into the right atrium to pick up the atricum pulse as a control signal for the circuit 30. For demand pacing, the surface electrode 32 may be used to pick up the ventricle pulse and suppress the trigger circuit in the manner taught for example by Keller U.S. Pat. No. 3,431,912 or Greatbatch U.S. Pat. No. 3,478,746. The physical size of the capsules which form the bodies is sufficiently small to permit long-term treatment, such as in the case of a child. The apparatus and method of the attachment and implanting is one which results in minimum discomfort to the patient. In the event of failure, the size of the pacemaker is sufficiently small to make it feasible to simply leave it in place and to insert a new one, although intravenous removal by catheter also is possible.

While the forms of apparatus herein described constitute preferred embodiments of the invention, it is to be understood that the invention is not limited to these precise forms of apparatus, and that changes may be made therein without departing from the scope of the invention.

Having thus described our invention, we claim:

1. A stimulator device for insertion in a living body, and capable of insertion in the heart, comprising a capsule having a generally cylindrical body portion including a positive pulsing electrode at its exterior surface, said body portion having in connection therewith means defining a negative pulsing stimulating electrode which is insulated from said positive electrode and has a surface portion exposed to form a leading end portion of the exterior surface of said capsule as it is applied to a body by transvenous or transarterial insertion, pulsing means connected to said electrodes having in immediate connection therewith a power source and means for activation thereof, and said capsule forming a housing containing the total of said pulsing means, power source and activating means to form threwith an integral unit having a fully contained power source and conditioned thereby to function free of outside leads or wires on placement thereof in a body by transvenous or transarterial insertion.

2. A device as in claim 1 wherein said power source includes a battery the function of which is determined by the biological load provided by the living body.

3. A device as in claim 2 wherein said battery is a nucleonic power source.

4. A device as in claim 2 wherein said battery is radioisotope fueled.

5. A device as in claim 2 characterized by said battery being contained within said capsule means forming a shield about said battery within said capsule, said battery being electrically connected with said pulsing means, and said electrode means being electrically connected with said battery and said pulsing means to form therewith a circuit in which the living body is incorporated to provide a biological load in said circuit.

6. In combination with the apparatus of claim 1, to guide the capsule to its desired location, a manipulator including plural elements for operative connection with engagement means provided on the outer surface of said capsule, a first of said elements constituting means connected with said engagement means for axially moving said capsule in the course of transvenous or transarterial insertion thereof and a second of said elements constituting a slip fit holding means positioning concentric with said moving means and having means for engaging said capsule to hold the same during the application to and release from said capsule of said moving means and said engaging means being operatively connected with said engagement means to effect a rotation of said capsule, if required.

7. Apparatus as in claim 6 wherein said plural elements include a third element mounting about said first and second elements for selective axial movement with respect thereto whereby to enable it to provide at least a partial sheath for said capsule.

8. A stimulator device as in claim 1 characterized by said capsule having a minimum overall length not substantially exceeding 30mm. and a peripheral configuration the maximum transverse dimension of which does not substantially exceed 8mm.

9. Apparatus as in claim 1 wherein said power source includes energy storing means and means for supplying energy to said storing means which is responsive to hemodynamic pressure produced thereon by the living body in which said capsule is inserted.

10. Apparatus as in claim 9 wherein said means for supplying energy to said storing means includes a portion of said capsule which is contractable and expansible in response to the application thereto and the release therefrom of hemodynamic pressure, and said expansible and contractable portion of said capsule has in connection therewith means responsive to the movement thereof to transmit the energy so produced to said energy storing means.

11. Apparatus as in claim 1 wherein said power source includes means defining a mass, means mounting said mass to provide for a periodic movement of said mass in response to a function of the living body and means in connection with said mounting means to transmit energy so produced to an energy storing means in connection therewith, which energy storing means is in operative connection with said pulsing means.

12. Apparatus as in claim 11 wherein said mounting means includes spring means.

13. Apparatus as in claim 12 wherein said spring means has in connection therewith a base including a permanent magnet.

14. Apparatus as in claim 12 wherein said spring means has a base including a piezoelectric crystal stressed by movement of said mass.

* * * * *

UNITED STATES PATENT AND TRADEMARK OFFICE
CERTIFICATE OF CORRECTION

PATENT NO. : 3,943,936
DATED : March 16, 1976
INVENTOR(S) : Ned S. Rasor and Joseph William Spickler It is certified that error appears in the above-identified patent and that said Letters Patent are hereby corrected as shown below:

Col. 1, line 17, "in" (second occurrence) is corrected to read -- by --;

line 64, "powe" is corrected to read -- power --.

Col. 2, line 20, "138" is corrected to read -- 238 --.

Col. 11, line 13, "atricum" is corrected to read -- atrium --;

line 48, "threwith" is corrected to read -- therewith --.

Signed and Sealed this

Sixth Day of July 1976

[SEAL]

Attest:

RUTH C. MASON
*Attesting Officer*

C. MARSHALL DANN
*Commissioner of Patents and Trademarks*